(12) United States Patent
Poteet et al.

(10) Patent No.: US 12,326,443 B2
(45) Date of Patent: Jun. 10, 2025

(54) DETECTING ANTIMICROBIAL SURFACES

(71) Applicant: B/E Aerospace, Inc., Winston Salem, NC (US)

(72) Inventors: Steven Poteet, Ashland, MA (US); Katherine Urena Pimentel, Winston-Salem, NC (US); Thomas Martz, Winston-Salem, NC (US); Irene Rexwinkle, Mill Creek, WA (US); Vijay V. Pujar, Rancho Santa Fe, CA (US); David Charles McConnell, Winston-Salem, NC (US)

(73) Assignee: B/E AEROSPACE INC., Winston Salem, NC (US)

( * ) Notice: Subject to any disclaimer, the term of this patent is extended or adjusted under 35 U.S.C. 154(b) by 697 days.

(21) Appl. No.: 17/476,169

(22) Filed: Sep. 15, 2021

(65) Prior Publication Data
US 2022/0091107 A1 Mar. 24, 2022

Related U.S. Application Data

(60) Provisional application No. 63/080,974, filed on Sep. 21, 2020.

(51) Int. Cl.
G01N 33/532 (2006.01)
A01N 55/00 (2006.01)
(Continued)

(52) U.S. Cl.
CPC ........... *G01N 33/532* (2013.01); *A01N 55/00* (2013.01); *C09D 5/14* (2013.01); *G01N 21/63* (2013.01);
(Continued)

(58) Field of Classification Search
CPC ......... A01N 55/00; C09D 5/14; C09D 5/1687
See application file for complete search history.

(56) References Cited

U.S. PATENT DOCUMENTS 9,206,382 B2    12/2015  Lant et al.
2003/0078441 A1*  4/2003  Zhao ................... C07D 409/14
                                                    549/60
(Continued)

FOREIGN PATENT DOCUMENTS

CN    109778390 A       5/2019
EP       3508554 A1 *   7/2019  .............. B01J 13/14
(Continued)

OTHER PUBLICATIONS

AEM 5772 Antimicrobial Product Label, obtained from https://www3.epa.gov/pesticides/chem_search/ppls/064881-00002-20180418.pdf, accessed Jul. 11, 2024 (Year: 2024).*
(Continued)

*Primary Examiner* — Zachary M Davis
(74) *Attorney, Agent, or Firm* — SNELL & WILMER L.L.P.

(57) ABSTRACT

A method includes depositing an antimicrobial material onto a surface of a substrate. The method includes binding a photochromic material to the antimicrobial material. Depositing the antimicrobial material and binding the photochromic material can include forming a mixture of the antimicrobial material and the photochromic material and depositing the mixture onto the surface of the substrate. It is also contemplated that depositing the antimicrobial material and binding the photochromic material can include first depositing the antimicrobial material onto the surface of the substrate and then depositing the photochromic material onto the antimicrobial material.

7 Claims, 4 Drawing Sheets

(51) Int. Cl.
  *C09D 5/14* (2006.01)
  *G01N 21/63* (2006.01)
  *G01N 33/569* (2006.01)

(52) U.S. Cl.
  CPC . G01N 33/56911 (2013.01); *G01N 2021/634* (2013.01)

(56) References Cited

U.S. PATENT DOCUMENTS

| | | | |
|---|---|---|---|
| 2009/0298967 A1* | 12/2009 | Taylor | C09D 175/04 523/122 |
| 2010/0240799 A1* | 9/2010 | Hofmann | A61K 8/8129 436/164 |
| 2017/0292068 A1 | 10/2017 | Kandapallil et al. | |

FOREIGN PATENT DOCUMENTS

| | | |
|---|---|---|
| EP | 3929569 A1 | 12/2021 |
| EP | 3936858 A1 | 1/2022 |
| KR | 20110002716 U | 3/2011 |
| WO | 2008157323 A1 | 12/2008 |

OTHER PUBLICATIONS

Extended European Search Report dated Feb. 11, 2022, issued during the prosecution of European Patent Application No. EP 21197837.4.

Elena Poverenov et al., Formation of Contact Active Antimicrobial Surfaces by Covalent Grafting of Quaternary Ammonium Compounds:, Colloids and Surfaces B: Biointerfaces, Elsevier Amsterdam, NL, vol. 169, pp. 195-205, May 25, 2018.

European Patent Office, European Office Action dated Nov. 22, 2024 in Application No. 21197837.4.

* cited by examiner

DETECTING ANTIMICROBIAL SURFACES

CROSS-REFERENCE TO RELATED APPLICATIONS

This application claims benefit of priority to U.S. Provisional Patent Application No. 63/080,974 filed Sep. 21, 2020, the content of which are incorporated herein by reference in its entirety.

BACKGROUND

1. Field

The present disclosure relates to antimicrobial coatings, and more particularly to systems and methods of detecting efficacy of antimicrobial coatings.

2. Description of Related Art

Surfaces in aircraft interior that are frequent touchpoints, e.g., aircraft seats, tray tables, magazine pouches, seat handles, luggage bins, and the like, may harbor microbes (viruses, bacteria, spores) that may be transferred between passengers. While surfaces are disinfected during regular cleaning, there is a need to maintain these surfaces free of microbes between scheduled cleaning.

The conventional techniques have been considered satisfactory for their intended purpose. However, there is an ever present need for improved systems and methods for keeping surfaces inherently microbe free to minimize transfer of microbes. This disclosure provides a solution for this need.

SUMMARY

A method includes depositing an antimicrobial material onto a surface of a substrate. The method includes binding a photochromic material to the antimicrobial material. Depositing the antimicrobial material and binding the photochromic material can include forming a mixture of the antimicrobial material and the photochromic material and depositing the mixture onto the surface of the substrate. It is also contemplated that depositing the antimicrobial material and binding the photochromic material can include first depositing the antimicrobial material onto the surface of the substrate and then depositing the photochromic material onto the antimicrobial material.

The antimicrobial material can include Si-QAC (3-(trimethoxysilyl) Propyldimethyl Octadecyl Ammonium Chloride). The photochromic material can include at least one of sulfonates, sulfates, carboxylates, acrylates, phosphates, and/or phosphonates. The photochromic material can include an anionic moiety. Binding the photochromic material to the antimicrobial material can include the anionic moiety binding to ammonium in the Si-QAC. The anionic moiety binding to ammonium in the Si-QAC can include the anionic moiety binding to a quaternary ammonium in respective spiked molecules of the Si-QAC.

The photochromic material can be an anionic die with absorbance near-UV which undergoes isomerization to become visible under near-UV illumination and remain invisible absent the near-UV illumination. The method can include illuminating the photochromic material to reveal if any of the antimicrobial material is compromised or missing. If any of the antimicrobial material is revealed by illumination to be compromised or missing, the method can include re-applying the antimicrobial material and re-applying the photochromic material.

An antimicrobial structure includes a substrate. An array of spiked molecules of antimicrobial material extend from a surface of the substrate. Photochromic material is bound to the spiked molecules. The substrate can include at least one of an aircraft seat surface, an aircraft tray table surface, an aircraft magazine pouch surface, an aircraft seat handle surface, an aircraft luggage bin surface, an aircraft overhead bin surface, an aircraft lavatory surface, an aircraft galley surface, and/or an aircraft cockpit surface.

An antimicrobial material includes a mixture of an antimicrobial material and a photochromic material. The antimicrobial material can be any antimicrobial material disclosed herein. The photochromic material can be any antimicrobial material disclosed herein.

An antimicrobial surface includes a substrate, a coating comprising an antimicrobial material deposited on the substrate, and a photochromic material bound on at least a portion of the antimicrobial substrate. The photochromic material can be deposited as an array. The photochromic material need be bound on only a portion of the antimicrobial material.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
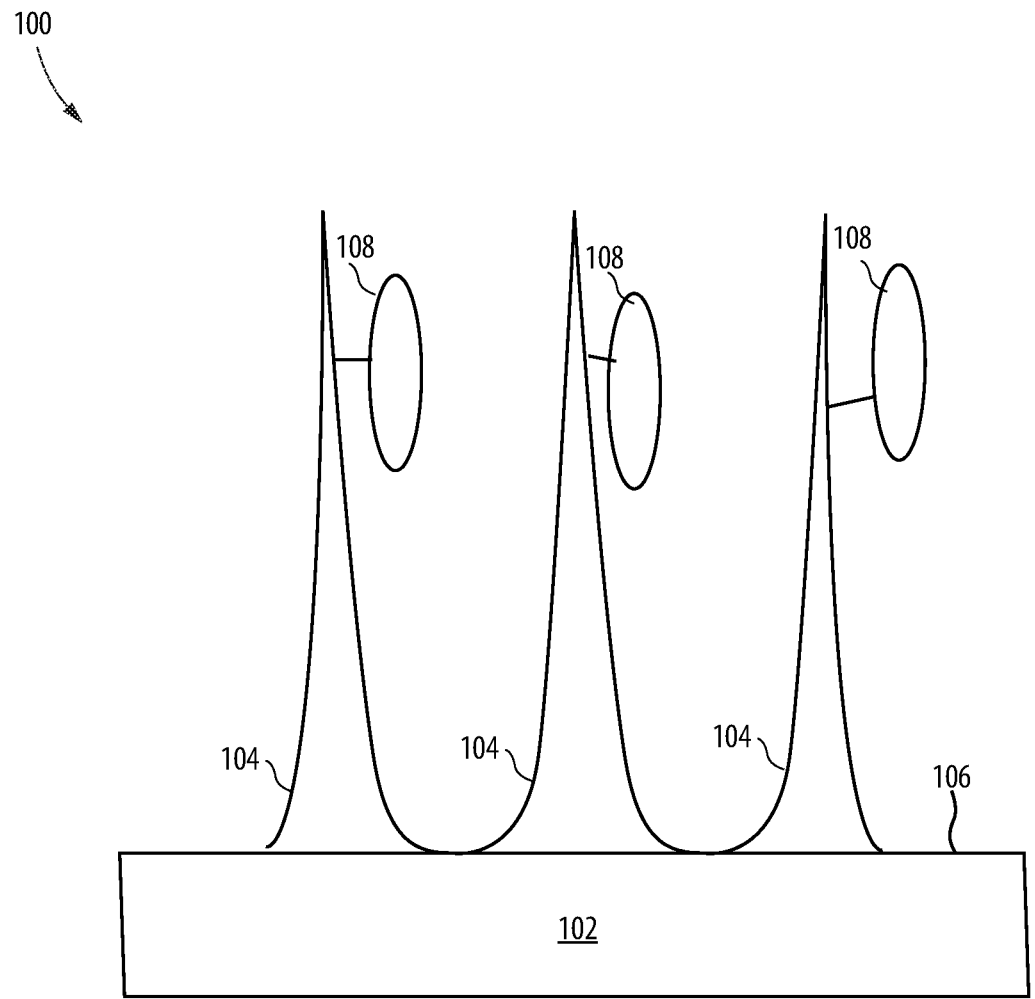
FIG. 1 is a schematic view of an embodiment of an antimicrobial structure constructed in accordance with the present disclosure, showing the spiked molecules of the antimicrobial material and the photochromic material bound to the spiked molecules.

Reference will now be made to the drawings wherein like reference numerals identify similar structural features or aspects of the subject disclosure. For purposes of explanation and illustration, and not limitation, a partial view of an embodiment of an antimicrobial structure in accordance with the disclosure is shown in FIG. 1 and is designated generally by reference character 100. Other embodiments of systems in accordance with the disclosure, or aspects thereof, are provided in FIGS. 2-4, as will be described. The systems and methods described herein can be used to provide antimicrobial surfaces that can be checked using an illuminator to confirm presence/efficacy of the antimicrobial surface.

Figure 4:
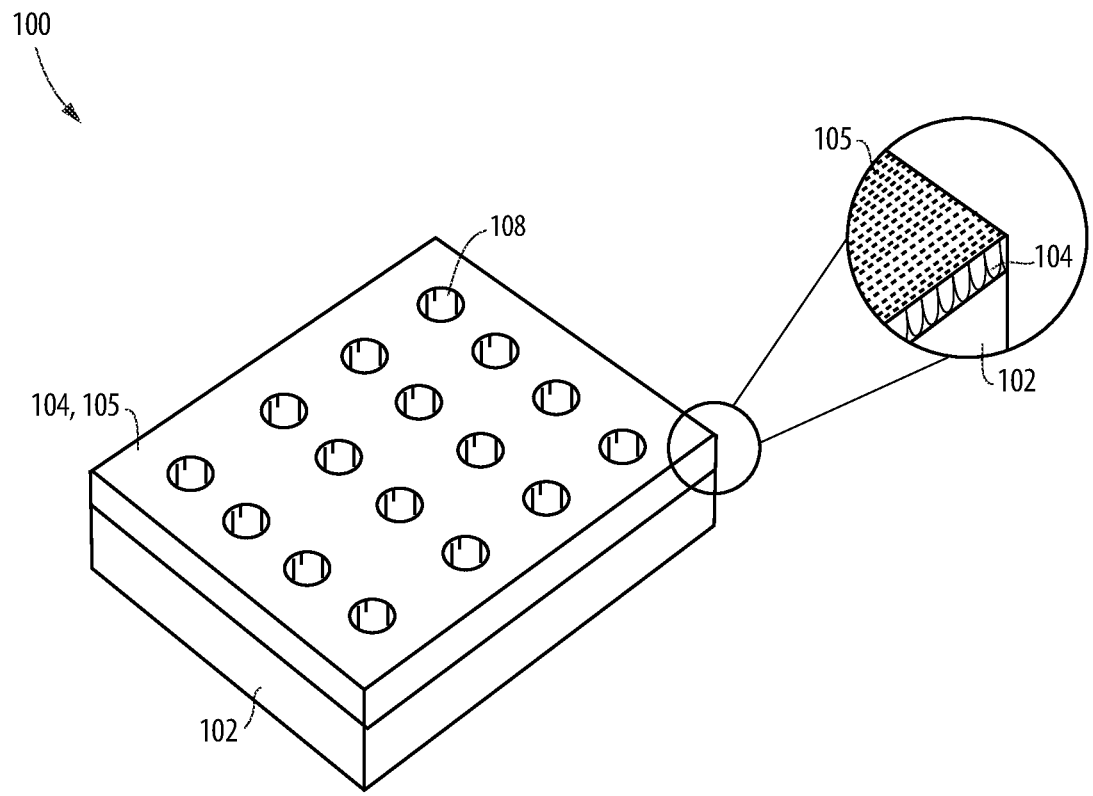
FIG. 4 is a schematic perspective view of the structure of FIG. 1, showing photochromic material deposited on the antimicrobial material in a pattern or array.

The antimicrobial structure 100 includes a substrate 102. An array of spiked molecules 104 of antimicrobial material 105 extend from a surface 106 of the substrate 102. Photochromic material 108 may be bound to at least a fraction of the spiked molecules 104. The substrate 102 can include at least one of an aircraft seat surface, an aircraft tray table surface, an aircraft magazine pouch surface, an aircraft seat handle surface, an aircraft luggage bin surface, an aircraft overhead bin surface, an aircraft lavatory surface, an aircraft galley surface, and/or an aircraft cockpit surface, or any other suitable surface. The photochromic material 108 need be bound on only a portion of the antimicrobial material 105 on the substrate 102, as shown in FIG. 4. The photochromic material 108 can be deposited as an array or pattern such as the pattern shown in FIG. 4 or any other suitable pattern including a decorative pattern.

Figure 2:
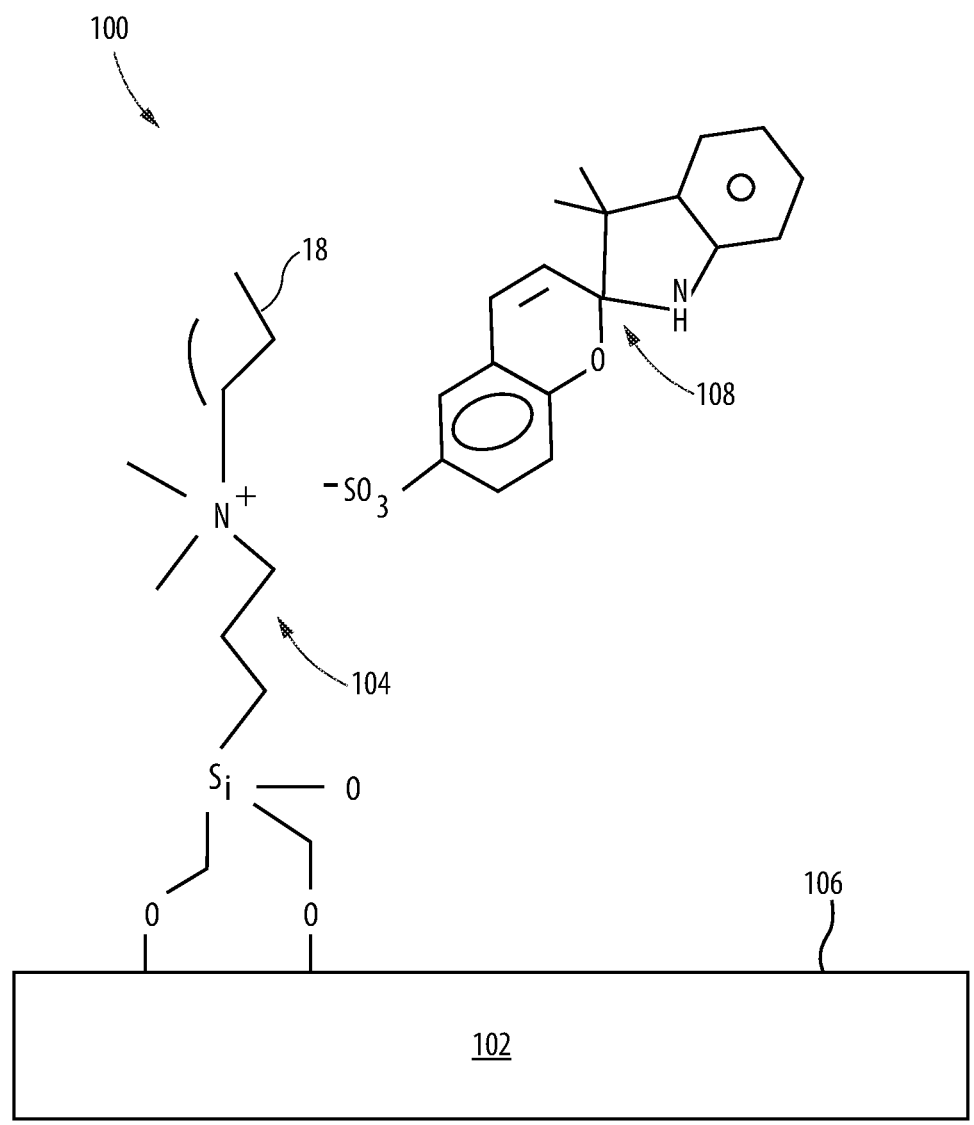
FIG. 2 is a schematic view of an example of the antimicrobial structure of FIG. 1, showing the molecular bond between one of the spiked molecules and the photochromic material.

As shown in FIG. 2, the antimicrobial material can include Si-QAC (3-(trimethoxysilyl) Propyldimethyl Octadecyl Ammonium Chloride). With respect to the photochromic material 108, it can be a dye with an anionic moiety. The anionic moiety allows the dye molecules to ionically bond to the cationic ammonium, e.g., the quaternary ammonium, portion of the antimicrobial spiked molecules 104. The photochromic material 108 can include spiropyrans (as shown in FIG. 2), indolino-naphthoxazines, diarylethenes, naphthopyrans, and/or spirooxazines. Examples of suitable anionic moieties for the antimicrobial material 108 include sulfonates, sulfates, carboxylates, acrylates, phosphates, phosphonates.

The photochromic material 108 is an anionic dye with absorbance near-UV which undergoes isomerization to become visible under near-UV illumination and remain invisible absent the near-UV illumination. The photochromic dye reacts differently than a fluorescent dye. Fluorescent dyes react by exciting an electron via light (typically UV), and the resulting falling electron emits light. In fluorescent dyes there is no structural change to the molecule. In a photochromic compound, the illumination actually results in temporary bond breaking (photoisomerism), and that breakage results in emitted light. The effect is illumination such as near-UV illumination can make the dye appear to have a visible color it does not have in the absence of the near-UV illumination. For aesthetics the surface 106 thus appears to be whatever color is desired unless the illumination is present. The antimicrobial function of the combined photochromic, antimicrobial material is not impacted by the bonding of the photochromic material 108 to the spiked molecules 104.

Figure 3:
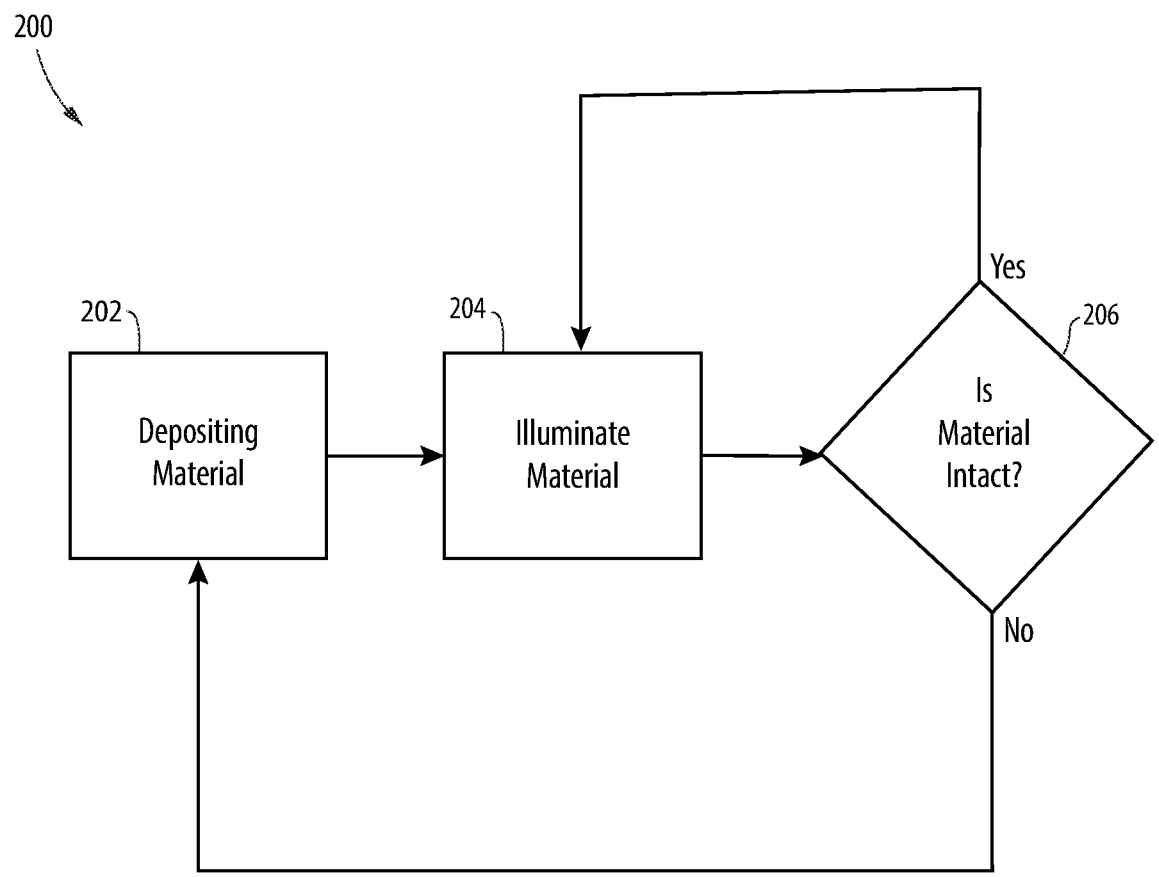
FIG. 3 is a schematic view of a method in accordance with the subject disclosure, showing a procedure for monitoring and maintaining the antimicrobial structure.

With reference now to FIG. 3, a method 200 includes depositing 202 an antimicrobial material onto a surface of a substrate, e.g. substrate 102 of FIG. 1. The method includes binding a photochromic material, e.g. photochromic material 108 of FIG. 1, to the antimicrobial material. The antimicrobial material can be formed into a mixture of the antimicrobial material and the photochromic material and the method can include depositing the antimicrobial, photochromic mixture onto the surface of the substrate. It is also contemplated that the antimicrobial material can be deposited onto the substrate first, and then the photochromic material can be deposited onto the antimicrobial material.

The method 200 can include illuminating 204 the photochromic material to reveal if any of the antimicrobial material is compromised or missing. For example, on an aircraft a crew member can shine a near-UV flashlight on surfaces to check the antimicrobial coatings. The photochromic color will show under illumination if the antimicrobial material is intact on a given surface. If any of the antimicrobial material is revealed by illumination to be compromised or missing, the method can include re-applying the antimicrobial material and re-applying the photochromic material. The checking by illumination and reapplication as needed can be repeated on a regular basis, as indicated by the decision box 204.

This disclosure provides for inspection at manufacture, coating quality, coverage, highly sensitive inspection of coating, which can be invisible when not under irradiation, and can optionally be premixed into a coating solution prior to application, potentially reducing additional labor. Simple inspection is possible under an illuminator, which can provide confidence about the efficacy of the antimicrobial function. The materials can be turned for specific colors/wavelengths for aesthetics.

The methods and systems of the present disclosure, as described above and shown in the drawings, provide for antimicrobial surfaces that can be checked using an illuminator to confirm presence/efficacy of the antimicrobial surface. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An antimicrobial structure comprising:
   a substrate;
   an array of spiked molecules of antimicrobial material extending from a surface of the substrate; and
   a photochromic material bound to the spiked molecules, wherein the photochromic material is an anionic dye with absorbance near-UV which undergoes isomerization to become visible under near-UV illumination and remain invisible absent the near-UV illumination and wherein the photochromic material includes at least one of spiropyrans, indolino-naphthoxazines, or diarylethenes.

2. The structure as recited in claim 1, wherein the substrate includes at least one of:
   an aircraft seat surface, an aircraft tray table surface, an aircraft magazine pouch surface, an aircraft seat handle surface, an aircraft luggage bin surface, an aircraft overhead bin surface, an aircraft lavatory surface, an aircraft galley surface, and/or an aircraft cockpit surface.

3. The structure as recited in claim 1, wherein the antimicrobial material includes Si-QAC (3-(trimethoxysilyl) Propyldimethyl Octadecyl Ammonium Chloride).

4. An antimicrobial material comprising:
   a mixture of an antimicrobial material and a photochromic material, wherein the photochromic material is an anionic dye with absorbance near-UV which undergoes isomerization to become visible under near-UV illumination and remain invisible absent the near-UV illumination and wherein the photochromic material includes at least one of spiropyrans, indolino-naphthoxazines, or diarylethenes.

5. An antimicrobial surface comprising:
   a substrate;
   a coating comprising an antimicrobial material deposited on the substrate;
   a photochromic material bound on at least a portion of the antimicrobial substrate, wherein the photochromic material is an anionic dye with absorbance near-UV which undergoes isomerization to become visible under near-UV illumination and remain invisible absent the near-UV illumination and wherein the photochromic material includes at least one of spiropyrans, indolino-naphthoxazines, or diarylethenes.

6. The antimicrobial surface as recited in claim 5, wherein the photochromic material is deposited as an array.

7. The antimicrobial surface as recited in claim 5, wherein the photochromic material is bound on only a portion of the antimicrobial material.

* * * * *